(12) United States Patent
Simonson et al.

(10) Patent No.: US 6,617,591 B1
(45) Date of Patent: Sep. 9, 2003

(54) METHOD FOR REMOTE DETECTION OF TRACE CONTAMINANTS

(75) Inventors: Robert J. Simonson, Cedar Crest, NM (US); Bradley G. Hance, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/004,921

(22) Filed: Dec. 3, 2001

(51) Int. Cl.[7] .......................... G01N 21/64; G01N 21/75
(52) U.S. Cl. ..................... 250/459.1; 436/172
(58) Field of Search ............................. 250/459.1, 302, 250/458.1; 436/166, 172, 56

(56) References Cited

U.S. PATENT DOCUMENTS

| | | | | |
|---|---|---|---|---|
| 4,651,010 A | * | 3/1987 | Javan ....................... | 250/458.1 |
| 4,876,206 A | * | 10/1989 | Sayer ......................... | 436/172 |
| 5,128,882 A | * | 7/1992 | Cooper et al. ........... | 250/458.1 |
| 6,025,200 A | * | 2/2000 | Kaish et al. ................. | 436/56 |
| 6,026,135 A | * | 2/2000 | McFee et al. ................ | 376/159 |
| 6,200,818 B1 | * | 3/2001 | Eigen et al. ................ | 436/172 |

OTHER PUBLICATIONS

Simonson, et al., "Remote Detection of Nitroaromatic Explosives in Soil using Distributed Sensor Particles," in *Detection and Remediation Technologies for Mines and Minelike Targets VI*, Proceedings of SPIE, vol. 4394, (2001) pp 879–889.

Measures, "Fundamentals of Laser Remote Sensing," Laser Remote Sensing: Fundamentals and Applications, Wiley–Interscience (1984), pp 1–79.

Williams, et al., "Design of Novel Iptycene–Containing Fluorescent," Polymers for the Detection of TNT, SPIE, vol. 3710 (1999), pp 402–408.

George, et al., "Progress of Determining the Vapor Signature of a Buried Landmine," SPIE, vol. 3710 (1999), pp 258–269.

Ia Grone, et al., "Landmine Detection by Chemical Signature Detection of Vapors of Nitroaromatic Compounds by Fluorescence Quenching of Novel Polymer Materials," SPIE, vol. 3710 (1999), pp 409–420.

* cited by examiner

*Primary Examiner*—Christopher W. Fulton
(74) *Attorney, Agent, or Firm*—Kevin W. Bieq

(57) ABSTRACT

A method for remote detection of trace contaminants in a target area comprises applying sensor particles that preconcentrate the trace contaminant to the target area and detecting the contaminant-sensitive fluorescence from the sensor particles. The sensor particles can have contaminant-sensitive and contaminant-insensitive fluorescent compounds to enable the determination of the amount of trace contaminant present in the target are by relative comparison of the emission of the fluorescent compounds by a local or remote fluorescence detector. The method can be used to remotely detect buried minefields.

13 Claims, 7 Drawing Sheets

METHOD FOR REMOTE DETECTION OF TRACE CONTAMINANTS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

The present invention relates to the remote detection of trace contaminants in a target area and, more particularly, to the detection of explosives by remote observation of the effect of explosive-signature compounds on the fluorescence of sensor particles applied to a suspect mined area.

Currently, there are no reliable methods for the remote detection of buried landmines and/or antipersonnel minefields. Geophysical sensors for landmine detection, such as electromagnetic induction sensors, magnetometers, and radar can exhibit high probabilities of detection but their performance is often limited by high false alarm rates due to "clutter" from objects with physical properties similar to those of the target mines.

The presence of explosive compounds in or above the soil can provide a useful discriminating signature for detection of buried mines or other unexploded ordnance. However, neither trace chemical detection methods ("sniffers") nor bulk methods (e.g., nuclear quadrupole resonance) are capable of standoff detection at ranges greater than a few meters. Additionally, trace chemical methods are limited by environmental fate and transport of explosive compounds in the minefield environment. The concentration of landmine signature compounds like trinitrotoluene (TNT) and dinitrotoluene (DNT) adsorbed on soils has been found to far exceed the equilibrium vapor concentration, while most of the transport of these explosives through soil occurs in the aqueous phase. M. Ia Grone et al., SPIE 3710, 401 (1999). The maximum measured concentrations of nitroaromatic compounds in surface soils above buried landmines have been reported to be as high as a part per million (about 1 mg/kg). However, laboratory measurements of vapor concentrations above similarly contaminated soils are many orders of magnitude lower. Thus, phase partitioning favors detection of adsorbed or aqueous compounds. Furthermore, the difficulty in detecting vapor from adsorbed explosives in the soil, in conjunction with the requirement for rapid sampling and analysis to maintain forward progress of a sensor, places severe requirements on the performance of vapor sensors. In particular, extremely low mass limits of detection are required for a trace chemical sensor to respond to the vapor over a buried landmine.

Significant investment has been made in developing remote optical methods (optical absorption and/or fluorescence light detection and ranging) for the detection of chemical- and bio-warfare agents. However, no similar methods currently exist for the remote detection of minefields, due to the low concentrations and lack of suitable spectral signatures for nitroaromatic explosives. Therefore, there remains a need for a reliable method of remote detection of buried minefields and/or antipersonnel minefields.

SUMMARY OF THE INVENTION

The present invention is directed to a method for the remote detection of trace contaminants in a target area, comprising applying to the target area sensor particles capable of preconcentrating the trace contaminant and having comprising a contaminant-sensitive fluorescent compound with optical emission that is sensitive to the presence of the trace contaminant; and detecting the optical emission of the contaminant-sensitive fluorescent compound with a detection means to determine the amount of trace contaminant present in the target area. The method further comprises adding a contaminant-insensitive fluorescent compound with optical emission that is insensitive to the presence of the trace contaminant to the sensor particles prior to applying the sensor particles to the target area. The contaminant-insensitive fluorescent compound provides an internal reference whereby the optical emission of the contaminant-sensitive fluorescent compound can be compared to the optical emission of the contaminant-insensitive fluorescent compound to determine the amount of trace contaminant present in the target area. The method further comprises exposing the target area to a mobile phase to facilitate the uptake of the trace contaminant by the sensor particles. The fluorescence detection can be done locally or remotely. Furthermore, the detection means can be a spectroscopic or imaging detector.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 2 shows the chemical formulas for fluorescent compounds that can be added to the sensor particles.

DETAILED DESCRIPTION OF THE INVENTION

The present invention relies on chemical to optical signal transduction through the use of sensor particles having a fluorescent signature that changes due to chemical reactions with the trace contaminant of interest. The sensor particles can be applied over the target area by air. Each sensor particle can essentially perform a chemical assay of its local environment and selectively uptake the trace contaminant. The uptake of the trace contaminant can thereby change the fluorescent signature of the sensor particles, the change being capable of remote optical detection. Ratiometric fluorescence sensing, whereby the emission of a contaminant-sensitive fluorescent compound in the sensor particle is compared to the emission of a contaminant-insensitive fluorescent compound in the sensor particle, enables the practical application of this method for field use. For sensor particles having favorable spectral signatures, remote trace contaminant sensing can be achieved by laser-induced-fluorescent Light Detection And Ranging (LIDAR). The method can be applied generally to the detection of trace contaminants in a target area. The method has been applied to the fluorescence detection of explosives in soil.

Preparation of the Sensor Particles

Figure 1:
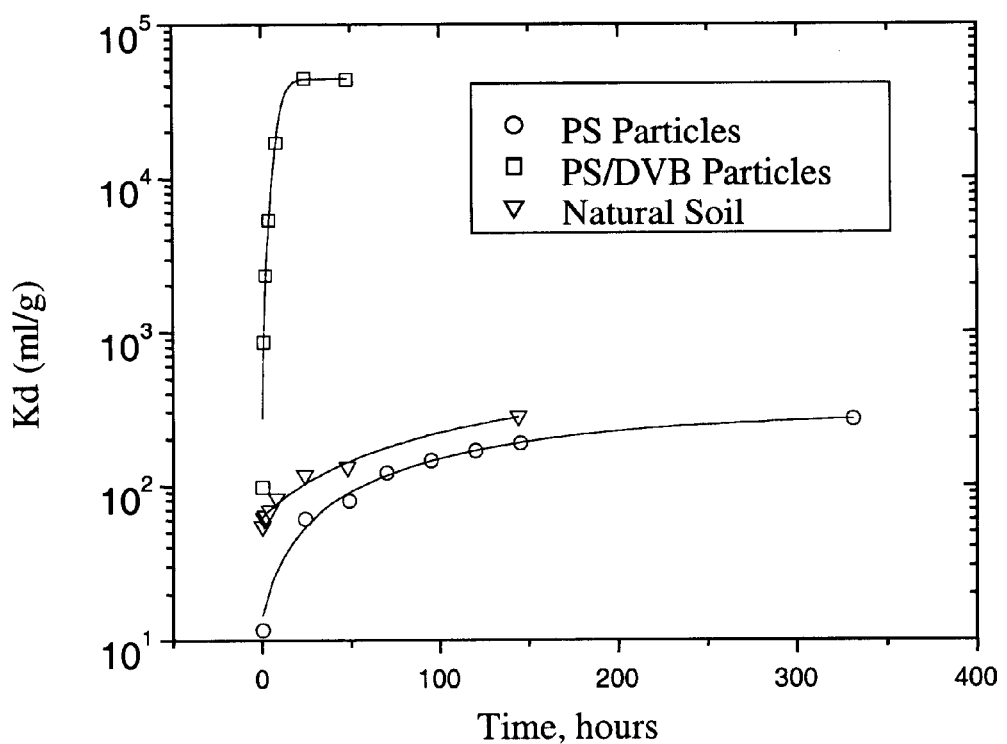
FIG. 1 shows a graph of the aqueous partition coefficients for TNT onto candidate polymeric sensor particles and soil.

Sensor particles preferably both absorb the trace contaminant from the local environment and exhibit changes in fluorescence due to the presence of the absorbed trace contaminant. The primary means for explosive transport in a soil environment is in the aqueous (soil water) phase. FIG. 1 shows the aqueous partition coefficients of TNT for candidate polymer sensor particles of polystyrene and polystyrene-divinyl benzene (PS/DVB) copolymer, and a sieved fraction (<100 mesh) of natural soil from a target minefield. Aqueous partition coefficients ($K_d$) for TNT onto the candidate polymer sensor particles were measured by agitating measured masses of particles with TNT solutions of known initial concentration and monitoring the drop in the aqueous concentration as the mixed phases approached equilibrium. The PS/DVB copolymer particles have a significantly larger $K_d$ than soil. The PS/DVB copolymer can therefore selectively absorb and preconcentrate TNT when sufficient water is present in the soil to provide a mobile phase.

Therefore, PS/DVB copolymer particles were selected as the sensor particles, due to their ability to absorb nitroaromatics, including TNT, from aqueous solution.

Figure 2A:
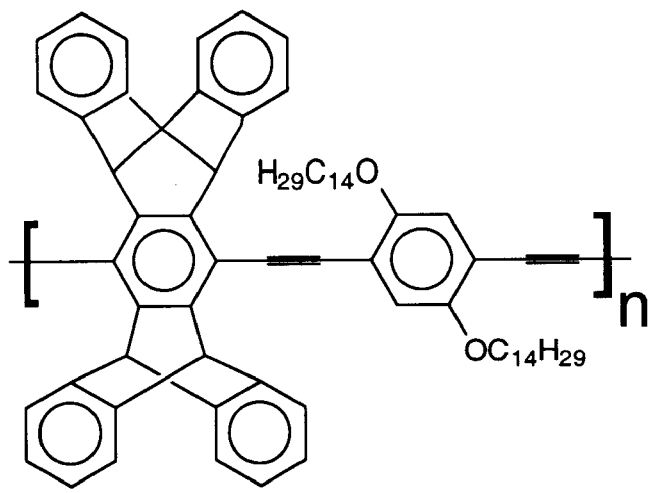
FIG. 2A shows the chemical formula for an iptycene-derived phenyleneethynylene polymer.

Nitroaromatic explosives exhibit strong ultraviolet absorption but low fluorescent quantum yields, with nonradiative deexcitation of excited states predominating over radiative emission. Therefore, direct detection of the trace contaminants by fluorescence can be inefficient. However, the sensor particles can be doped with an appropriate fluorescent compound to sense the presence of the trace contaminant. Emission from the fluorescent compound may be enhanced or quenched due to the presence of the trace contaminant. Synthetic fluorescent polymers have been developed whose emission is strongly quenched in the presence of nitroaromatics. V. E. Williams et al., SPIE Proceedings 3710, 402 (1999). In particular, fluorescent optical sensitivity of the sensor particles to nitroaromatics can be achieved by dissolving a small proportion (about $10^{-4}$ by mass) of an iptycene-derived phenyleneethynylene polymer, hereinafter referred to as C14, into the PS/DVB copolymer particles. The C14 polymer is shown in FIG. 2A. The C14 polymer exhibits a very sensitive response to the presence of nitroaromatic explosives, due to strong oxidative quenching of the highly delocalized excited state of the C14 polymer. When dissolved in the PS/DVB sensor particle matrix, the C14 polymer exhibits an absorption maximum at approximately 430 nm wavelength, and an emission maximum at approximately 460 nm.

Quenching of the emission of the fluorescent compound in the sensor particle in the presence of the trace contaminant can be measured locally, with a field-portable spectrometer; in a laboratory; or remotely, with LIDAR. For minefield detection of explosives, remote detection is preferable. However, standoff measurements of fluorescence from particles applied to the ground over a minefield present several difficulties. The 460 nm wavelength emission of the C14 polymer is in the visible region of the electromagnetic spectrum, such that a change in emission intensity due to TNT-induced quenching of the sensor particle emission would present a dark signal on a bright background.

Figure 2B:
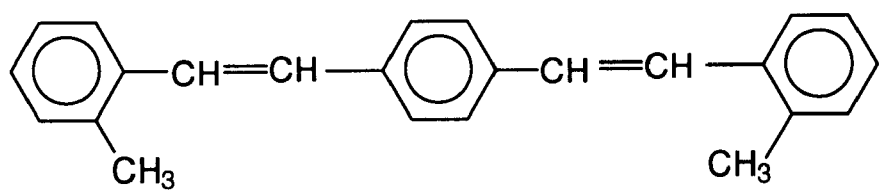
FIG. 2B shows the chemical formula for p-bis(o-methylstyryl)-benzene.
Figure 3:
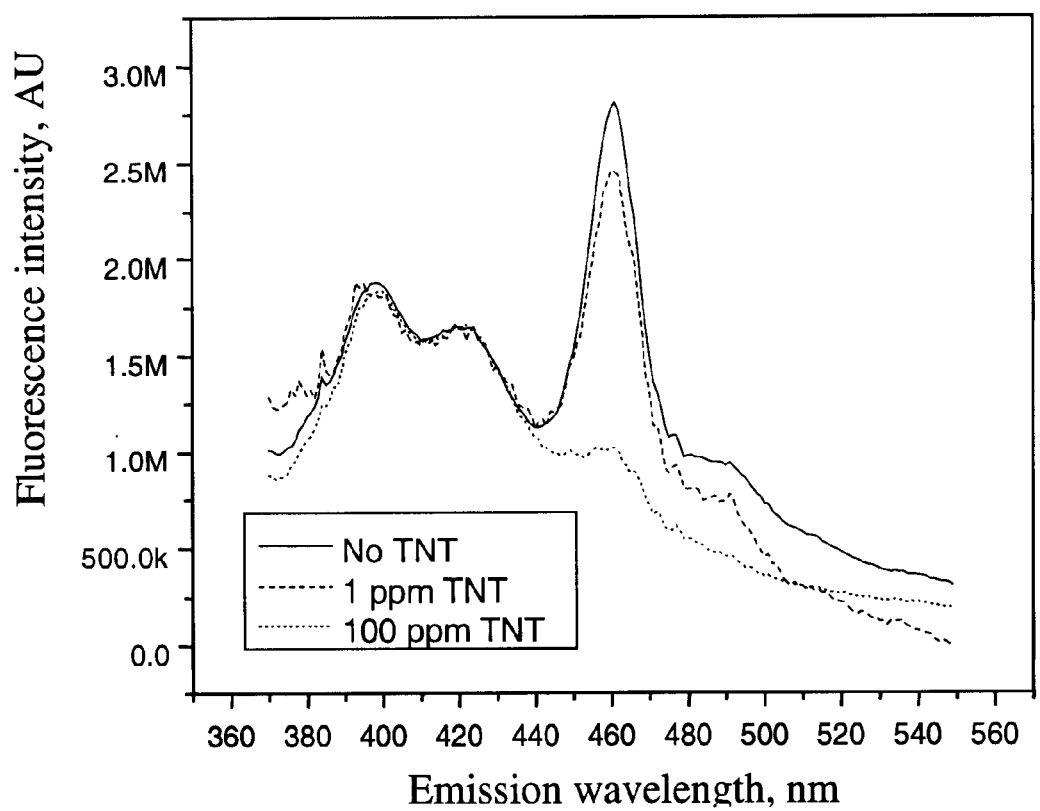
FIG. 3 shows a graph of the normalized emission spectra of sensor particles from wetted contaminated- and uncontaminated-soil taken with a laboratory emission spectrometer.
Figure 4:
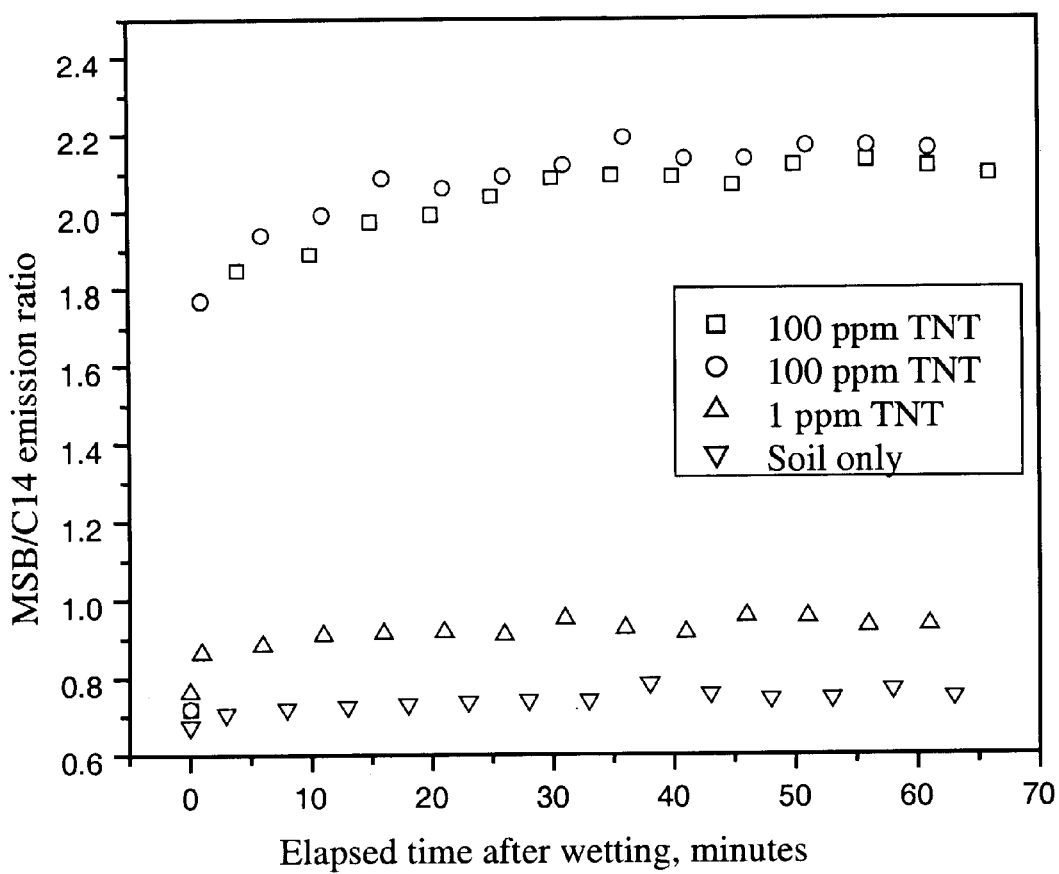
FIG. 4 shows an elapsed time graph of the MSB/C14 emission ratio from sensor particles applied to various soils after wetting.
Figure 5:
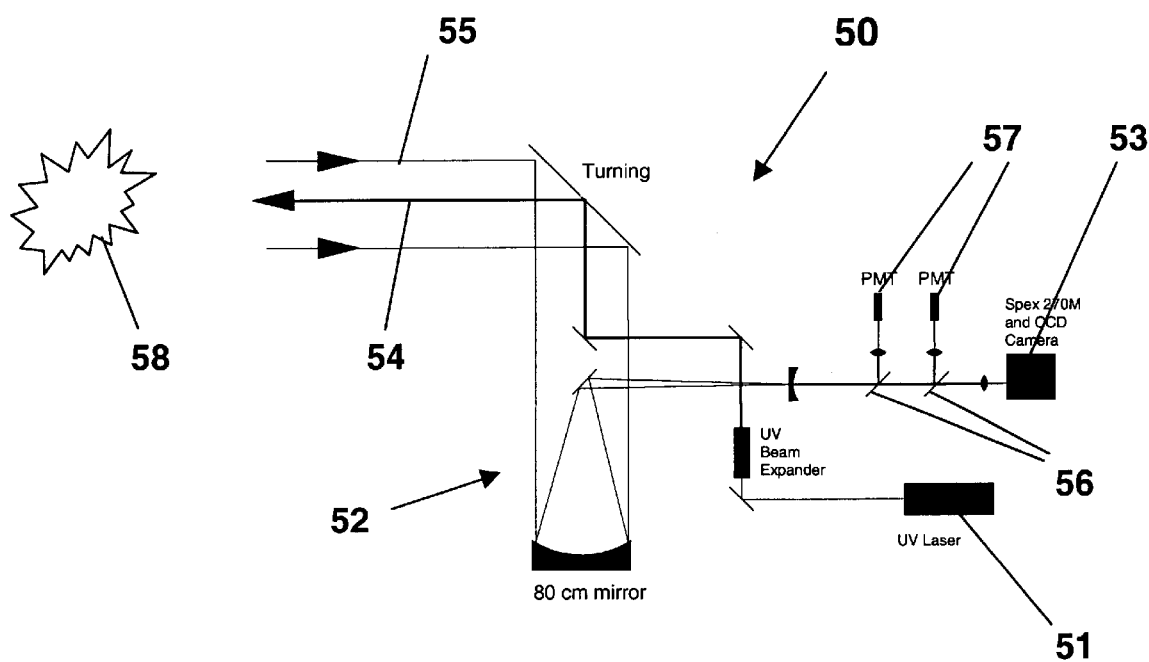
FIG. 5 shows a schematic illustration of a Light Detection And Ranging (LIDAR) instrument.
Figure 6:
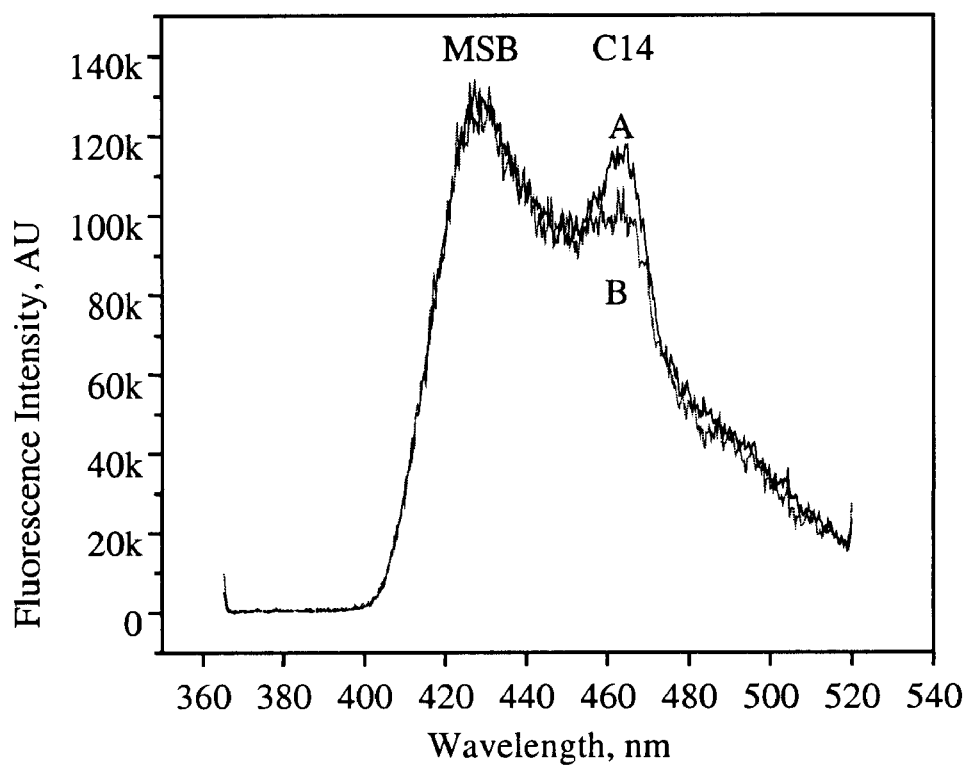
FIG. 6 shows a graph of the normalized emission spectra of sensor particles from an uncontaminated soil sample and a soil sample contaminated with 100 ppm TNT collected with the LIDAR instrument at 500 m range.
Figure 7:
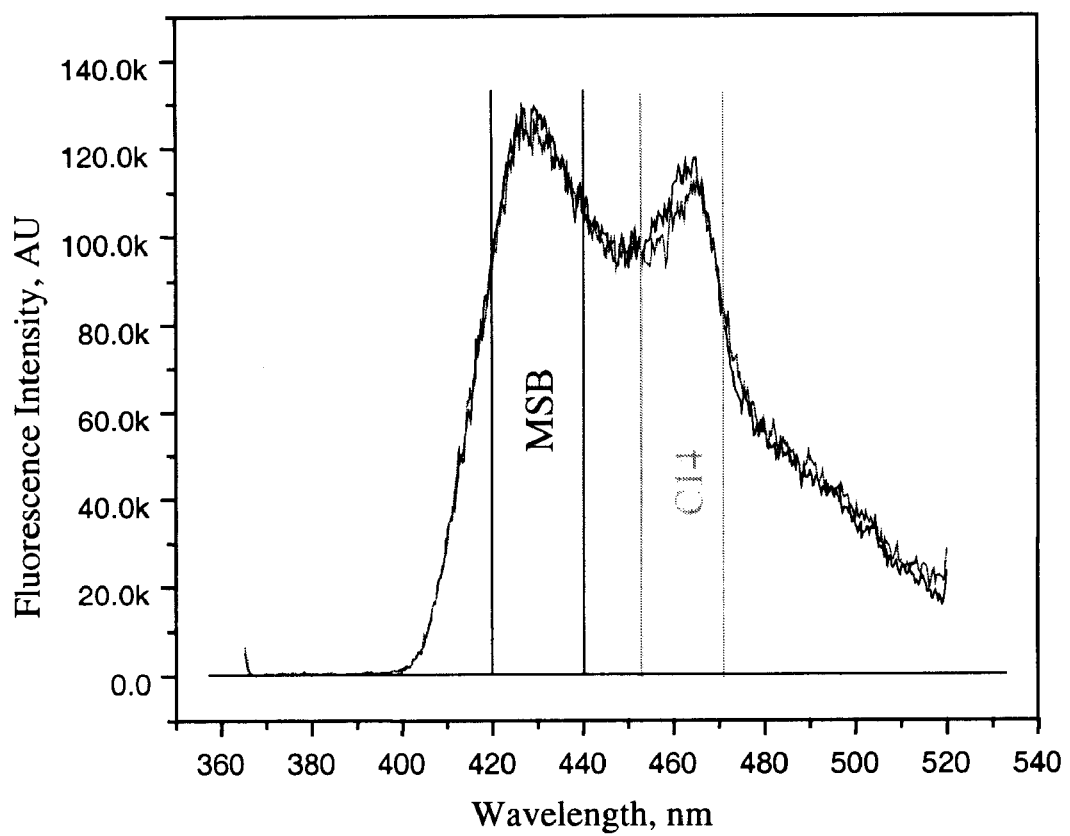
FIG. 7 shows a graph of the normalized emission spectra of sensor particles from an uncontaminated soil sample and a soil sample contaminated with 1 ppm TNT collected with the LIDAR instrument at 500 m range.

In addition, the decrease in emission due to nitroaromatic quenching should preferably be resolvable from variations from other factors, such as uneven distribution of the sensor particles. A preferred method for remote detection is to "spray" the suspected mined areas with a suspension of sensor particles in water. The water provides a mobile phase for preconcentration of the TNT in the sensor particles prior to the fluorescence measurement. With spraying, the distribution of sensor particles per unit area in such a mined area may not be sufficiently uniform for landmine detection based on spatial variation of the fluorescent signal from the TNT-sensitive fluorescent compound in the sensor particle alone. Therefore, a TNT-insensitive fluorescent compound, p-bis(o-methylstyryl)-benzene (MSB), shown in FIG. 2B, can be added in the formulation of the sensor particles. The MSB is substantially unaffected by the presence of the nitroaromatic trace contaminants. In the ratiometric fluorescence sensing method of the present invention, the TNT-insensitive MSB emission can be used to normalize the TNT-sensitive C14 emission signal at 460 nm for variations in background illumination, pump illumination, and particle coverage. In addition to providing an internal reference standard, MSB provides for efficient energy transfer of the excitation radiation to the TNT-sensitive fluorescent compound, C14. This is because MSB has an absorption maximum in PS/DVB at about 360 nm wavelength and exhibits multiple emission maxima at about 400 nm and 420 nm wavelengths, near the excitation maximum for C14.

Sensor particles for TNT detection can be prepared from 200–400 mesh, 80% styrene/20% divinylbenzene copolymer beads. 600 $\mu$l of chloroform, 100$\mu$l of 0.338 mg/ml C14 polymer in toluene, and 36 $\mu$l of 25 $\mu$g/ml MSB in toluene can be combined with 0.3 g of PS/DVB beads in a glass scintillation vial, which can then be capped and allow to stand overnight. After this mixing and incubation time, the processing solvents can be removed in a rotary evaporator. Once the mixture has dried to the point where free solid clumps of material are observed, the vial can be removed from the rotary evaporator, two 1/8" steel balls can be added, and a small amount (0.2–0.5 ml) of chloroform can be used to wash material from the sides of the vial. The rotary evaporation step can be repeated. When the material in the vial appears to be dry, the vial can be removed from the rotary evaporator, capped and shaken with the steel balls to break up agglomerated particles. The processed material can be visually inspected under ambient light and ultraviolet light for uniformity of color and particle size. Following visual inspection, fluorescence emission spectra can be obtained to verify the proper MSB/C14 ratio.

TNT and DNT-contaminated natural soil samples were prepared to evaluate the detection method of the present invention using sensor particles prepared by the above described process. Samples of uncontaminated surface soil were collected and sieved through a 2-mm screen and dried at 140° C. for 7 days. Analytical grade DNT crystals were added to the soil in a one-gallon paint can to a concentration of about 10 mg/kg. The container was placed on a roller mill for 4 is days at about 30 rpm. Water was added to bring the soil to about 0.01 g water/g soil, and the DNT-contaminated soil samples were placed in an oven at 110° C. for 4 days to distribute the explosive. The container was then removed from the oven and placed on the roller mill for 1 day. Recrystallized military grade TNT was used to prepare stock TNT-contaminated soil samples in a similar fashion, to a concentration of about 100 mg/kg. To create lower soil concentrations, the stock soil was serially diluted with clean dry soil. The contaminated soils were assayed after preparation using solvent elution and gas chromatography, to verify concentration and homogeneity.

The sample holders for the evaluations were simple aluminum cylinders, 2.5 inches in diameter and 1 inch deep, with a 2-inch diameter uv quartz window on one end face and a removable cover on the other. For practical use of this method in the field, the mass of sensor particles applied per unit area across a suspected minefield should preferably be kept low. A concentration of 1 mg of sensor particles per square centimeter results in a reasonable total mass requirement of 100 kg of sensor particles per hectare of target area (100 kg/10,000 $m^2$). Therefore, contaminated samples were prepared by sprinkling about 1 mg/$cm^2$ of the sensor particles by hand on the inner face of the quartz window. Approximately 10 g of soil was then placed in the sample holder.

Local Fluorescence Detection

FIG. 3 shows normalized fluorescence spectra from contaminated and uncontaminated soils obtained with a conventional single-grating emission spectrometer having an arc lamp excitation source. The excitation light at 350 nm was normally incident (90 degrees from the sample plane) and fluorescence was collected at an angle of 22.5 degrees from the surface normal. The spectra were taken after both contaminated and uncontaminated soil samples were wetted with about 0.3 g HPLC grade water per gram of soil. The spectra indicate quenching of the emission of the C14 polymer at 460 nm and 490 nm relative to the unquenched MSB emission peaks at 400 nm and 420 nm, due to the presence of TNT in the contaminated sample. Similar spectra acquired for sensor particles on contaminated but dry soil 15 samples did not exhibit significant C14 quenching. Thus, the presence of water as a mobile phase can facilitate transport of the explosive from the surface of the soil to the sensor particles. FIG. 4 shows the ratio of intensities of the MSB emission at 420 nm to the emission of the C14 polymer at 460 nm, plotted as a function of elapsed time following addition of water to the soil samples. This MSB/C14 emission ratio increases with elapsed time after wetting, as the TNT is transported from the soil through the water phase to the sensor particles, thereby causing the TNT to quench the C14 emission. The maximum increase in the signal occurs within 2–3 minutes after water is added to the system and reaches an asymptotic value within approximately 1 hour, indicating the rapid transport of TNT in the aqueous phase.

Remote Fluorescence Detection

FIG. 5 shows a schematic illustration of the LIDAR instrument 50 that can be used to obtain remote fluorescence measurements of the contaminated soils 58 by UV laser-induced fluorescence. The LIDAR instrument 50 comprises a tunable UV laser source 51, a collection telescope 52, and a range- and spectrally-resolved detector 53. R. M. Measures, Laser Remote Sensing: Fundamentals and Applications, Wiley-Interscience (New York) 1984. The fluorescent light 55 from the sensor particles containing the mixed MSB+C14 compounds can be optically pumped with a 355 nm wavelength excitation pulse 54 from a tripled Nd:YAG laser 51. The excitation pulse 54 can be and transmitted to the contaminated soil 58 coaxially with the receiver field of view. The Nd:YAG laser 51 provides for a relatively lightweight, compact, rugged, pulsed excitation source for interrogation of the sensor particle fluorescence in the field. Backscattered light and fluorescent return light 55 can be gathered by the collection telescope 52 comprising an 80-cm-diameter primary mirror that collimates the collected return light 55 to an about 2-cm-diameter beam. Two uncoated quartz beamsplitters 56 send a fraction (about 15%) of the return light 55 to two photomultiplier tubes 57 which can provide time-resolved elastic and fluorescence data.

The remainder of the collected return light 55 can be sent to the spectrometer 53 with an charge-coupled-device (CCD) detector to allow time-gated spectrally resolved analysis of the sensor particle fluorescence. For the detection of the explosive-contaminated soils, the CCD detector can be electronically gated with a gate width of 100 ns and a starting gate coincident with the prompt scattered light return, due to the short emission lifetime of the MSB and C14 fluorescence. A long-pass optical filter can be used to block the elastically scattered light from the spectrometer and enhance the signal-to-noise of the laser-induced-fluorescence light. Typically, from 300 to 1000 excitation laser shots can be integrated on the CCD detector before readout. The excitation laser pulse rate can be 30 Hz, resulting in integration times of 10–33 seconds per collected spectrum.

To evaluate the method of the present invention for remote detection in the field, contaminated soil samples and uncontaminated samples, with sensor particle coverage of about 1 mg/$cm^2$, and which were wetted with about 0.3 g water/gram soil, were placed at a standoff range of 500 meters from the LIDAR instrument 50. The laser excitation beam 54 of the LIDAR instrument 50 has a nominal diameter of approximately 8 inches at 500 m range. At this range, the excitation beam 54 had a mean of 2.1 mJ per excitation pulse incident on the 2" diameter soil samples.

FIG. 6 compares normalized spectra obtained from an uncontaminated soil sample and a contaminated soil sample, containing 100 ppm TNT. Backscattered incident light and the background spectra from pure soil were subtracted from both samples. The key fluorescence emission peaks at 420 nm (due to the MSB) and 460 nm (due to the C14 polymer) are both easily resolved. The decrease in the C14 emission peak at 460 nm relative to the MSB emission peak at 420 nm indicates the quenching of the C14 emission due to TNT. Thus, the presence of 100 ppm TNT in the contaminated soil samples can be easily detected by the remote LIDAR instrument.

FIG. 7 shows similarly normalized emission spectra for an uncontaminated soil sample and a contaminated soil sample, containing 1 ppm TNT. Statistical analysis of the ratios of the integrated intensity in the MSB and C14 emission peaks indicate that contaminated soils containing 1 ppm TNT can be remotely detected by the LIDAR instrument at the 98% confidence level.

The LIDAR instrument 50 is spectrally resolving, but is not an imaging instrument. Signal-to-noise (SNR) calculations were performed for an imaging fluorescence instrument, using parameters for a commercially available intensified CCD array detector and laser excitation source, with a 30 cm fluorescence collection aperture. An interference filter with a 10 nm bandpass centered at 460 nm can be used to enhance the SNR for emission from the C14 polymer in the sensor particles. In addition, the time-gated fluorescence return light can be integrated from about 1000 excitation pulses of a 30 mJ/pulse laser at 355 nm. With an excitation pulse rate of 30 Hz, the integration time can be about 30 seconds. The imaging fluorescence instrument can have a useful SNR at a standoff range of a kilometer, for images of a 50 m diameter target area with a 5 cm nominal pixel resolution at the target. This pixel resolution is expected to be necessary to resolve signatures of antipersonnel mines. A stationary or a ground-vehicle mounted optical measurement platform designed to acquire fluorescence images at more modest standoff range (e.g., 10 m) can have much less severe optical and tracking design requirements than the long-range imaging fluorescence instrument described above.

The embodiments of the present invention have been described as a method for remote detection of trace contaminants in a target area. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for the remote detection of trace contaminants in a target area, comprising:
    a) applying sensor particles to the target area, the sensor particles capable of preconcentrating the trace contaminant and having a contaminant-sensitive fluorescent compound with optical emission that is sensitive to the presence of the trace contaminant and a contaminant-insensitive fluorescent compound with optical emission that is insensitive to the presence of the trace contaminant;
    b) detecting the optical emission of the contaminant-sensitive fluorescent compound and the optical emission of the contaminant-insensitive fluorescent compound with a detection means; and
    c) comparing the optical emission of the contaminant-sensitive fluorescent compound to the optical emission of the contaminant-insensitive fluorescent compound to determine the amount of trace contaminant present in the target area.

2. The method of claim 1, further comprising exposing the target area to a mobile phase prior to step b).

3. The method of claim 2, wherein the mobile phase is water.

4. The method of claim 1, wherein the contaminant-sensitive fluorescent compound comprises an iptycene-derived phenyleneethynylene polymer.

5. The method of claim 2, wherein the contaminant-insensitive fluorescent compound comprises p-bis(o-methylstyryl)-benzene.

6. The method of claim 1, wherein the target area comprises soil.

7. The method of claim 6, wherein the sensor particles comprise styrene/divinylbenzene copolymer.

8. The method of claim 1, wherein the sensor particles comprise polymer.

9. The method of claim 1, wherein the trace contaminant comprises a nitroaromatic compound.

10. The method of claim 9, wherein the trace contaminant comprises trinitrotoluene or dinitrotoluene.

11. The method of claim 1, wherein the detection means is a laser-induced-fluorescence instrument.

12. The method of claim 11, wherein the detection means is a light detection and ranging instrument.

13. The method of claim 11, wherein the detection means is an imaging fluorescence instrument.

* * * * *